(12) United States Patent
Kohno (10) Patent No.: US 7,318,806 B2
(45) Date of Patent: Jan. 15, 2008

(54) ULTRASOUND ENDOSCOPE

(75) Inventor: Shinichi Kohno, Saitama (JP)

(73) Assignee: Fujinon Corporation, Saitama (JP)

( * ) Notice: Subject to any disclaimer, the term of this patent is extended or adjusted under 35 U.S.C. 154(b) by 650 days.

(21) Appl. No.: 10/685,497

(22) Filed: Oct. 16, 2003

(65) Prior Publication Data

US 2004/0082883 A1    Apr. 29, 2004

(30) Foreign Application Priority Data

Oct. 18, 2002    (JP)  ............................. 2002-304505

(51) Int. Cl.
*A61B 8/00*    (2006.01)
*A61B 1/00*    (2006.01)

(52) U.S. Cl. ...................... 600/463; 600/127; 600/129

(58) Field of Classification Search ................ 600/439, 600/459, 461, 462–471, 104, 110, 113, 127, 600/129, 139, 175–176
See application file for complete search history.

(56) References Cited

U.S. PATENT DOCUMENTS

| 4,605,009 | A | * | 8/1986 | Pourcelot et al. | ............ | 600/109 |
| 4,757,819 | A | * | 7/1988 | Yokoi et al. | ................. | 600/156 |
| 4,763,662 | A | * | 8/1988 | Yokoi | .......................... | 600/461 |
| 5,471,988 | A | * | 12/1995 | Fujio et al. | ................... | 600/439 |
| 5,492,126 | A | * | 2/1996 | Hennige et al. | ............ | 600/439 |
| 5,499,630 | A | * | 3/1996 | Hiki et al. | ................... | 600/461 |
| 5,873,828 | A | * | 2/1999 | Fujio et al. | ................. | 600/439 |
| 6,149,598 | A | * | 11/2000 | Tanaka | ....................... | 600/462 |

(Continued)

FOREIGN PATENT DOCUMENTS

| DE | 37 16 954 | 11/1987 |
| DE | 100 18 673 | 1/2000 |
| EP | 0 123 594 | 10/1984 |
| JP | 2002-238906 | 8/2002 |

*Primary Examiner*—Francis J. Jaworski
(74) *Attorney, Agent, or Firm*—Oblon, Spivak, McClelland, Maier & Neustadt, P.C.

(57) ABSTRACT

A rigid tip end section which is connected to an angle section at the fore distal end of an insertion instrument of an ultrasound endoscope is housed in a casing which can be split into a main casing and a separable head block to facilitate maintenance and service of internal component parts of the rigid tip end section. An ultrasound transducer is accommodated in a front side portion of the main casing, while endoscopic observation means including an illumination means and an optical image pickup means are fitted in an inclined wall rising obliquely upward on the rear side of the ultrasound transducer. An outlet opening of a biopsy channel outlet passage is located between the ultrasound transducer and the endoscopic observation means. The main casing is adapted to accommodate the ultrasound transducer and its wiring, while the separable head block is adapted to accommodate at least part of component parts of the endoscopic observation means. The main casing and the separable head block are joined with each other through joint wall portions provided along split lines at the opposite lateral sides and at the front side thereof. A foremost one of angle rings of the angle section is detachably fitted on base end portions of the main casing and separable head block to retain these parts in a fixedly connected state.

20 Claims, 8 Drawing Sheets

U.S. PATENT DOCUMENTS

| | | | |
|---|---|---|---|
| 6,171,249 B1 * | 1/2001 | Chin et al. | 600/461 |
| 6,224,555 B1 * | 5/2001 | Ouchi | 600/439 |
| 6,238,336 B1 * | 5/2001 | Ouchi | 600/160 |
| 6,390,973 B1 * | 5/2002 | Ouchi | 600/113 |
| 6,409,666 B1 * | 6/2002 | Ito | 600/439 |
| 6,461,304 B1 * | 10/2002 | Tanaka et al. | 600/462 |

* cited by examiner

ULTRASOUND ENDOSCOPE

BACKGROUND OF THE INVENTION

1. Field of the Art

This invention relates to an ultrasound endoscope which is capable of both endoscopic and ultrasound examinations in body cavities, and more particularly to an ultrasound endoscope which is arranged to facilitate maintenance and service such as inspection, repair and replacements of internal component parts within a rigid tip end section at the distal end of an insertion instrument of an ultrasound endoscope.

2. Prior Art

Generally, ultrasound endoscopes are provided with an endoscopic observation means including an illumination window and an observation window on a rigid tip end portion at a distal end of an elongated insertion instrument along with an ultrasound examination means such as an ultrasound transducer. After introducing the insertion instrument into a body cavity, an intracavitary site of interest is firstly examined by the endoscopic observation means, and then the ultrasound examination means is used to further examine tissues in a diseased portion or a suspicious portion which has been spotted as a result of the endoscopic examination. In many cases, the so-called biopsy channel is provided in and through the endoscopic insertion instrument for forceps or a high frequency surgical or biopsy instrument to be introduced into a body cavity and operated under observation through the endoscopic observation means or for a puncture needle or other puncture instrument to be operated under observation through ultrasound scan images.

Connected to the base end of the insertion instrument of the ultrasound endoscope is a manipulating head assembly to be gripped by an operator at the time of endoscopic or ultrasound examination. Various operation control buttons and levers are provided on the manipulating head assembly. The insertion instrument has an elongated flexible body which can be bent easily along the shape of a path of insertion, and an angle section and a rigid tip end section are successively connected to the fore end of the elongated flexible body. The above-mentioned endoscopic observation means, ultrasound examination means and biopsy channel are provided on the rigid tip end section. Accordingly, by operating the manipulating head assembly to turn the angle section in an upward, downward, rightward or leftward direction, the rigid tip end section can be turned into an arbitrary direction.

As described above, the endoscopic observation means, ultrasound examination means and biopsy channel are mounted on the rigid tip end section which constitutes a distal end portion of the endoscopic insertion instrument. The ultrasound transducer which constitutes an ultrasound scan means is classified into either a mechanical scan type or an electronic scan type depending upon scan mode. In the case of an electronic scan type, the ultrasound transducer is constituted by a large number of transducer elements which are arrayed in a predetermined direction. At the time of an electronic scan, the transducer elements are driven successively one after another or transducer elements in a number of transducer element groups are successively driven to obtain echo signals.

On the other hand, the endoscopic observation means is largely composed of an illumination window in which a light emitting end of an illumination light guide is located, and an observation window in which a lens tube of an optical objective lens system is mounted. A solid-state image sensor device (or a light incident end of an image light guide) is located at the focus of the optical objective lens system. The optical objective lens system and the solid-state image sensor device are assembled together and provided as an image pickup assembly unit. Further, a biopsy channel, i.e., a passage for biopsy and surgical instruments, is generally constituted by a flexible tube which is bendable within the flexible body portion and angle section of the insertion instrument. A passage way leading to an outlet opening of the biopsy channel is bored through the rigid tip end section at the distal end of the insertion instrument. A connector pipe is fitted in the outlet passage way and a fore end portion of the flexible biopsy channel tube is connected to a base end of the connector pipe which is projected by a predetermined length from the proximal end of the rigid tip end section.

In laying out the various component parts of the endoscopic and ultrasound examination means on the rigid tip end section at the fore distal end of the insertion instrument, it has been known in the art to locate the ultrasound transducer at the distal end of the rigid tip end section, with ultrasound transducer elements arrayed in a convexly curved shape in the axial direction of the rigid tip end section. The observation window of the endoscopic observation means is provided in a sloped surface rising gradually upward toward the rear end of the rigid tip end section from the proximal end of the ultrasound transducer mount portion. Illumination windows are provided on the opposite lateral sides of the observation window. The biopsy channel is opened at a position between the ultrasound transducer mount portion and the observation window of the endoscopic observation means. Ultrasound endoscopes having the component parts of the endoscopic and ultrasound examination means laid out in this manner are known in the art, for example., from Japanese Laid-Open Patent Application 2002-238906.

In connecting a rigid tip end section to an angle section of an endoscopic insertion instrument, it is usually the case to connect the rigid tip end section separably to the angle section which is constituted by a series of flexibly connected rings. For this purpose, a foremost ring of the angle section is fitted and fixed on a proximal end portion of the rigid tip end section. An outer skin layer of the angle section is extended to a position beyond and forward of the foremost ring, and securely fixed on the rigid tip end section by line wrapping and an adhesive agent. The reason why the rigid tip end section is separably connected to the angle section is to make the maintenance and service of the component parts of the endoscopic and ultrasound examination means feasible, that is to say, to permit inspection, repair and replacements of internal component parts of the rigid tip end section.

In this regard, as already mentioned hereinbefore, an ultrasound transducer is mounted on the rigid tip end section. Wires from the respective ultrasound transducer elements on an ultrasound transducer assembly are led out from the transducer assembly and passed through the angle section and the elongated flexible main body portion of the insertion instrument and connected to corresponding wiring members in the manipulating head assembly of the endoscope. Further, signal lines of the endoscopic observation means, that is to say, signal lines which are connected from the solid-state image sensor device and led out from the image pickup assembly unit are also passed and extended through the angle section and the flexible body portion of the insertion instrument along with a bundle of fiber optics of the light guide which transmits illumination light to the illumination windows. Furthermore, a tube which serves as a biopsy channel is also passed through the angle section and the flexible main body and extended as far as the manipulating head assembly of the endoscope.

Generally, in the case of an ultrasound endoscope with an electronic scan type ultrasound transducer, it is the ultrasound transducer which is most expensive among the various component part which make up the ultrasound endoscope. Nevertheless, it has been extremely difficult to repair the ultrasound transducer when it is damaged or in the event of malfunctioning. That is to say, it has been virtually impossible to carry out maintenance and service on the ultrasound transducer. In contrast, it is relatively easy to replace the solid-state image sensor device and its wiring, the light guide and the biopsy channel tube when damaged.

Therefore, when the rigid tip end section is detached from the angle section, the jobs of maintenance and service have been limited to the solid-state image sensor device and its wiring, the light guide and the biopsy channel tube. Above all, internal surfaces of the biopsy channel tube are susceptible to damages since the biopsy channel is often used for insertion of puncture instruments with a sharp-pointed puncture needle. Further, breakage could occur to the signal lines from the solid-state image sensor device.

In order to enhance the resolution of ultrasound images, it is necessary for an ultrasound endoscope with an electronic scan type ultrasound transducer to increase the number of ultrasound transducer elements and to use a wiring system involving a considerably increased number of wiring connections. Therefore, when the rigid tip end section is detached and pulled away from the angle section to repair or replace a certain component part, difficulties are often encountered in separating the repairing or replacing component part from other component parts which are densely packed in the rigid tip end section of the insertion instrument. Therefore, it has been extremely difficult and troublesome to inspect, repair or replace a particular component part separately from other densely packed component parts, without damaging other component parts. Especially, in case the ultrasound transducer and the wiring to the transducer are made detachable or separable from the rigid tip end section to facilitate maintenance and service jobs on component parts other than the ultrasound transducer and its wiring, the construction of the rigid tip end section will become too complicate and will become a great obstacle to the maintenance and service.

Besides, at the time of relocating an image pickup assembly unit on the rigid tip end section of the insertion instrument, it is necessary to adjust its position in the rotational or radial direction. Further, regarding the biopsy channel, the biopsy channel tube is extended axially through the insertion instrument to a point immediately on the proximal side of the rigid tip end section and connected to a bent connector pipe which is fitted in a forwardly upturned exit passage in the rigid tip end section. Accordingly, the connector pipe has particular directionability in bending direction. It follows that the lens tube of the optical objective lens system as well as the connector pipe has to be securely and firmly fixed in position by application of an adhesive after adjusting its position relative to the rigid tip end section. Therefore, the applied adhesive has to be stripped off to take out the optical image pickup assembly unit and the biopsy channel from the rigid tip end section for maintenance and service. On such an occasion, there are increased possibilities of damaging other component parts which happen to be in the close proximity.

SUMMARY OF THE INVENTION

In view of the foregoing situations, it is an object of the present invention to provide an ultrasound endoscope having a rigid tip end section at the distal end of an insertion instrument housed in a casing which can be split into a main casing and a separable head block to facilitate maintenance and service of internal component parts of the rigid tip end section.

It is another object of the present invention to provide an ultrasound endoscope having a rigid tip end section at the distal end of an insertion instrument to accommodate an ultrasound scanner means along with an endoscopic observation means, the rigid tip end section being housed in a casing which can be split into a main casing adapted to accommodate component parts of the ultrasound scanner means fixedly therein and a separable head block adapted to accommodate at least part of component parts of the ultrasound observation means releasably to permit repair or replacements of the component parts of the endoscopic observation means separately of and without causing damages to component parts of the ultrasound scanner means.

According to the present invention, in order to achieve the above-stated objectives, there is provided an ultrasound endoscope having a rigid tip end section connected to a fore end of an angle section at the distal end of an insertion instrument for accommodating an ultrasound transducer along with endoscopic observation means including an illumination means and an optical image pickup assembly unit; the ultrasound transducer being accommodated in a front portion of a generally tubular casing of the rigid tip end section, the endoscopic observation means being fitted in a sloped wall section provided on the casing on the rear side of the ultrasound transducer and inclined obliquely upward in the rearward direction, and an outlet opening of a biopsy channel outlet passage opened in the casing at a position between the endoscopic observation means and the ultrasound transducer: characterized in that: the casing of the rigid tip end section is separable into a main casing adapted to accommodate entire parts of the ultrasound transducer and a separable head block adapted to accommodate at least part of component parts of the endoscopic observation means and separably joined with the main casing; joining wall portions are provided along longitudinal split lines at opposite lateral sides of the main casing and the separable head block as well as along a transverse split line on the rear side of the ultrasound transducer; a foremost ring member of angle rings in the angle section is removably fitted on a circular ring fitting surface provided around joined base end portions of the main casing and the separable head block; and a fore end of an outer skin layer of the angle section is extended forward beyond the ring fitting surface and fixedly anchored on a circular outer skin layer anchor surface provided around joined base end portions of the main casing and the separable head block on the front side of the ring fitting surface.

According to the present invention, the rigid tip end section of the insertion instrument is housed in a casing which can be split into a main casing and a separable head block. The main casing is adapted to accommodate an ultrasound transducer assembly fixedly therein, while the separable head block is adapted to accommodate at least part of component parts of an optical image pickup system of the endoscopic observation means. In this instance, the separable head block of the rigid tip end section is adapted either to accommodate all of an optical image pickup assembly unit including an optical objective lens system and a solid-state image sensor device along with a light guide and an illumination window fitted with a diffuser lens in front of a light emitting end of the light guide or to accommodate only part of these component parts. Alternatively, the optical image pickup unit assembly, light guide and diffuser lens are partly provided on the main casing and partly provided on the separable block in such a way that they are assembled together and fixed in position within the casing when the main casing and the separable block are joined together.

Any way, the separable block is adapted to be joined with the main casing through joining wall portions which are provided along longitudinal split lines at its opposite lateral sides as well as along a transverse split line provided at a position on the rear side of the ultrasound transducer which is accommodated in a front side portion of the casing. Consequently, when the separable head block is detached from the main casing, at least the ultrasound transducer and its wiring remain on the side of the main casing in an intact state, while other component parts of the rigid tip end section are separated from the main casing in an exposed state partly together with the separable head block. In this regard, joint wall portions of 11 the main casing and the separable head block can be arranged to accommodate, for example, a lens tube of an objective lens system of the optical image pickup assembly unit therebetween in such a way that the lens tube comes out in a free state when the separable head block is detached from the main casing. Considering convenience in actual maintenance and service works, it is desirable to arrange the split lines in such a way as to let the optical image pickup assembly unit or a connector pipe of a biopsy channel comes out separately and independently of other component parts when the separable head block is detached from the main casing.

The separable head block is joined with the main casing along longitudinal split lines at its opposite lateral sides and a transverse split line at its front end. In joining the separable block and the main casing together, it is necessary to join them together through joining wall portions which restricts relative movements in both axial and radial directions. After joining the separable head block with the main casing, a foremost one of angle rings of the angle section may be fitted on base end portions of the joined main casing and separable head block to fix the separable block in position relative to the main casing. Otherwise, desirably interlocking or interference surfaces are provided on the joining wall portions to block spontaneous movements of the separable head block relative to the main casing in axial, radial and lateral directions and to retain the main casing and separable block in the joined state more stably. As an example of interlocking surfaces, there may be provided joining wall portions with projections and recesses which are brought into interlocking engagement to restrict relative movements of the main casing and the separable head block in axial and radial directions when the separable head block is joined with the main casing. However, the interlocking engagement of joining wall portions may not be effective for restricting backward movements of the separable head block relative to the main casing. The movements of the separable head block in this direction can be restricted by the foremost ring member of the angle section. Therefore, an annular ring fitting surface substantially of the same diameter as the inside diameter of the foremost ring member of the angle section is formed around base end portions of the main casing and the separable head block when the latter is joined with the former. After fitting the foremost ring member on the annular ring fitting surface, the main casing and the separable head block are separably fixed to each other by the use of a removable fixation means, for example, by threading thereinto a number of set screws through the foremost ring member. More particularly, in such a case, it is necessary to use at least two screws, one screw for stopping the foremost ring member relative to the main casing and another screw for stopping the foremost ring member relative to the separable head block.

When the rigid tip end section is assembled by joining the separable head block with the main casing and fitting and fixing the foremost angle ring on base end portions of the joined main casing and the separable head block, it becomes necessary to keep the internal space of the rigid tip end section in a hermetically sealed state. Joined portions between the main casing and the separable head block can be sealed up by the use of seal material, preferably by applying resilient seal material like rubber between and around joined portions. The applying seal material is not necessarily required to have adhesive properties. However, seal material with a weak adhesive power may be applied if desired in consideration of machining accuracy of the main casing and the separable head block. An outer skin layer of the angle section can be utilized in forming a hermetical seal between the foremost angle ring and the ring fitting portions of the main casing and the separable head block. Normally, the outer skin layer of the angle section has resiliency and is stretchable in axial and radial directions. For forming a hermetical seal around the ring fitting portions, the fore end of the outer skin layer is extended forward beyond the position of the foremost angle ring and fixedly anchored in position on joined base end portions of the main casing and separable head block, for example, by the use of line wrapping and an adhesive. In this case, the internal space of the rigid tip end section can be sealed up completely.

Interior surfaces of a biopsy channel tube which constitutes a major part of a biopsy channel within the insertion instrument are susceptible to damages because the biopsy channel is often used for introduction of sharp-pointed instruments like a puncture needle. Therefore, arrangement can be made in such a way that the biopsy channel comes out independently and separately of other component parts when the separable head block is detached from the main casing. In this case, a biopsy channel outlet passage on the rigid tip end section is tubular in shape and inclined obliquely upward in the forward direction or toward an outlet opening of the biopsy channel. The tubular biopsy channel outlet passage can be longitudinally split into upper and lower halves. In a case where the biopsy channel outlet passage is inclined over its entire length, the split line is also inclined obliquely. In a case where the biopsy channel outlet passage is arranged in a bent shape, rising obliquely upward from a base end portion which is extended in the axial direction of the insertion instrument, the split line is bent in the same way as the biopsy channel outlet passage and consists of an inclined portion and an axial portion.

As the upper and lower halves of the split biopsy channel outlet passage, semi-circular grooves are formed on the meeting side of the separable head block and the main casing, respectively, and a connector pipe of a predetermined length is fitted between upper and lower semi-circular grooves to connect the biopsy channel tube with the biopsy channel outlet passage on the rigid tip end section. In this case, upon detaching the separable head block from the main casing, the connector pipe comes out of the split biopsy channel outlet passage. Therefore, the biopsy channel tube which is connected with the connector pipe can be easily taken out independently and separately of other internal component parts for replacement or for other purposes. The connector pipe which is fitted in the biopsy channel outlet passage retained in a restricted state against movements in axial and rotational directions. As fixation meas for this purpose, a set of a stopper projection and a key groove or notch may be provided between the connector pipe and the biopsy channel outlet passage. In this regard, projections or prongs which are provided on the circumferential surface of the connector pipe may be brought into engagement with notches which are provided on the upper and lower semi-circular grooves on the meeting side of the separable head block and the main casing. Since the connector pipe contains a bent portion, the just-mentioned fixation means becomes unnecessary in a case where the bent portion of the connector pipe is immovably fitted in the biopsy channel outlet passage.

In some cases, there may arise a necessity for replacing the optical image pickup assembly unit of the endoscopic observation means which is fitted within an endoscopic observation window. Therefore, arrangements may be made in such a way that the optical image pickup assembly unit comes out separately and independently of other internal components when the separable head block is detached from the main casing of the rigid tip end section. The optical image pickup assembly unit has a lens tube for an objective lens system, which should be fixedly mounted on the rigid tip end section. A lens tube fitting hole which is inclined obliquely upward in the forward direction is provided on the rigid tip end section to accommodate the lens tube of the optical image pickup unit assembly. This inclined lens tube fitting hole can also be arranged as a split type, and can also be formed by joining arcuate upper and lower semi-circular grooves which are provided on the separable head block and the main casing. The lens tube is gripped in the lens fitting hole upon joining the upper and lower semi-circular grooves one on the other. The lens tube in the lens tube fitting hole can be locked in axial and rotational directions by the use of fixation means similar to the stopper projection and key groove or notch as described hereinbefore in connection with the connector pipe of the biopsy channel.

The above and other objects, features and advantages of the present invention will become apparent from the following particular description of the invention, taken in conjunction with the accompanying drawings which show by way of example some preferred embodiments of the invention. Needless to say, the present invention is not limited to particular forms shown in the drawings.

DESCRIPTION OF PREFERRED EMBODIMENTS

Figure 1:
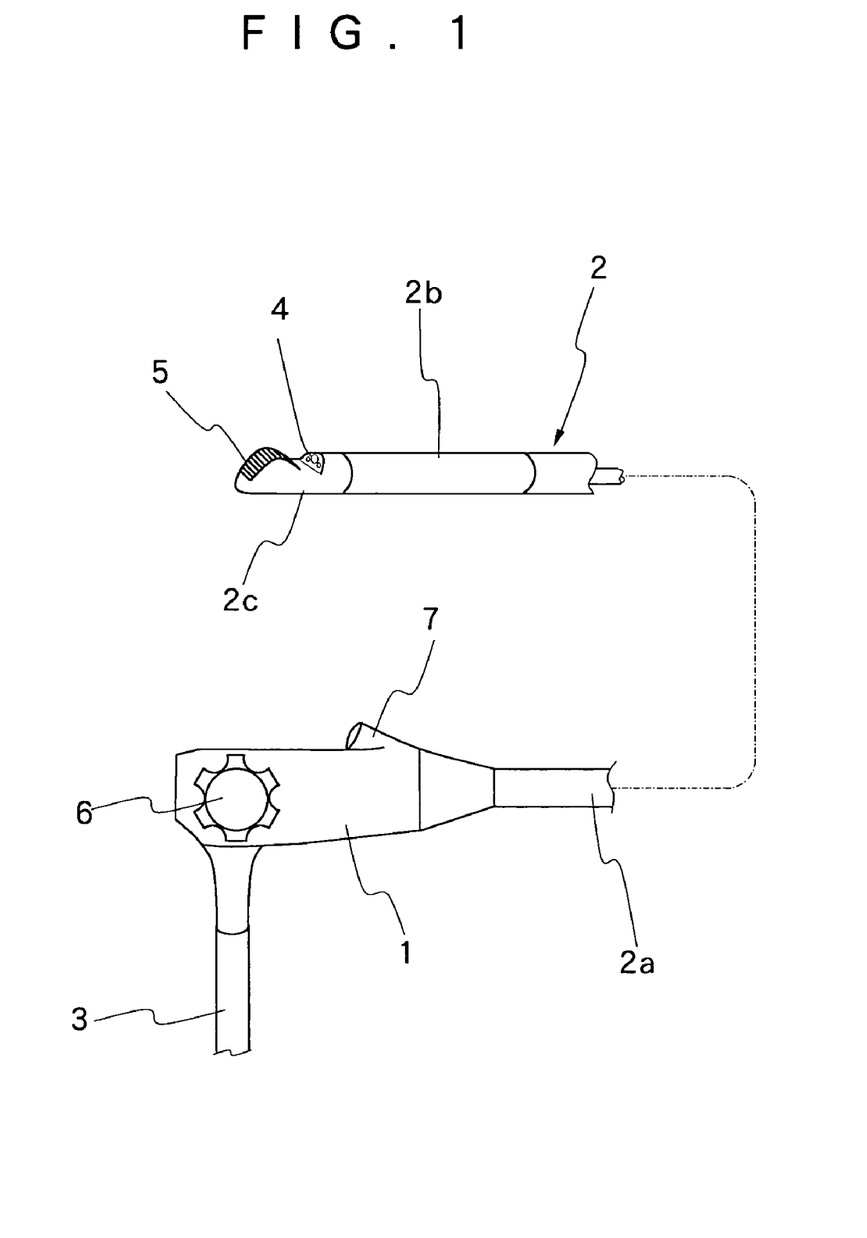
FIG. 1 is a schematic partly cutaway view of an ultrasound endoscope, showing general layout of the ultrasound endoscope.

Hereafter, the present invention is described more particularly by way of its preferred embodiments with reference to the accompanying drawings. Referring first to FIG. 1, there is schematically shown general layout of a typical ultrasound endoscope in which the present invention has been advantageously incorporated. In this figure, indicated at 1 is a manipulating head assembly to be gripped by an operator, at 2 an insertion instrument to be introduced into a body cavity of a patient, and at 3 a universal cable. From proximal to fore end, the insertion instrument 2 is composed of an elongated flexible body section 2a, an angle section 2b and a rigid tip end section 2c. The flexible body section 2a has a flexible body structure which is bendable in arbitrary directions along a path of insertion toward a patient's body cavity. The rigid tip end section 2c has a rigid structure to support thereon an endoscopic observation means 4 along with an ultrasound examination means 5. The angle section 2b is provided between the flexible body section 2a and the rigid tip end section 2c and manipulated by an angle section operating means 6 on the manipulating head assembly 1 to turn the rigid tip end section into a desired direction. Further, as described in greater detail hereinafter, an exit opening 29 of a biopsy channel is provided on the rigid tip end section 2c. Although not shown in the drawings, other buttons and switches are provided on the manipulating head assembly 1 for controlling the operation of the endoscope.

Figure 2:
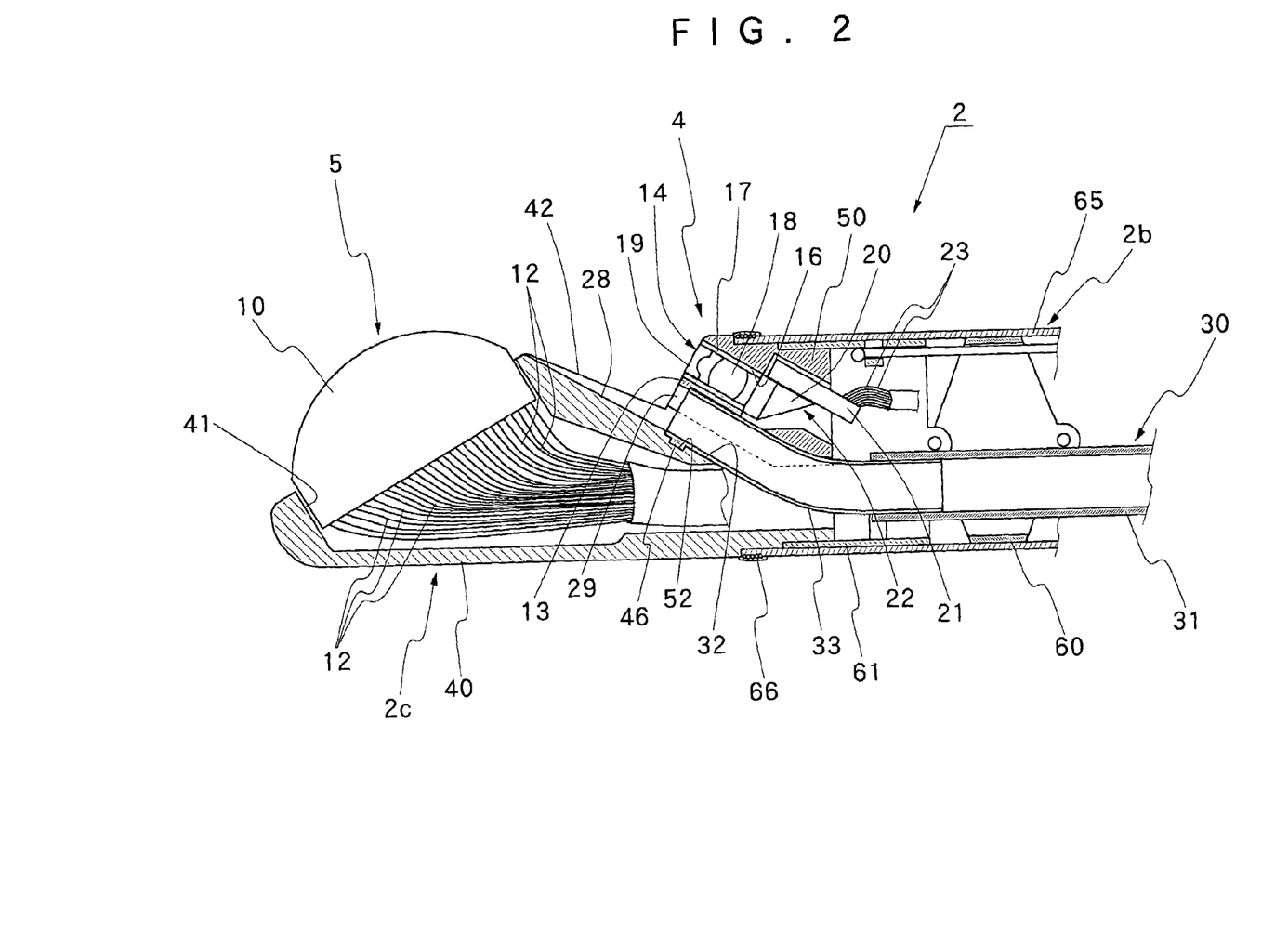
FIG. 2 is a longitudinal sectional view of a rigid tip end section of an insertion instrument of the ultrasound endoscope according to an embodiment of the present invention.
Figure 3:
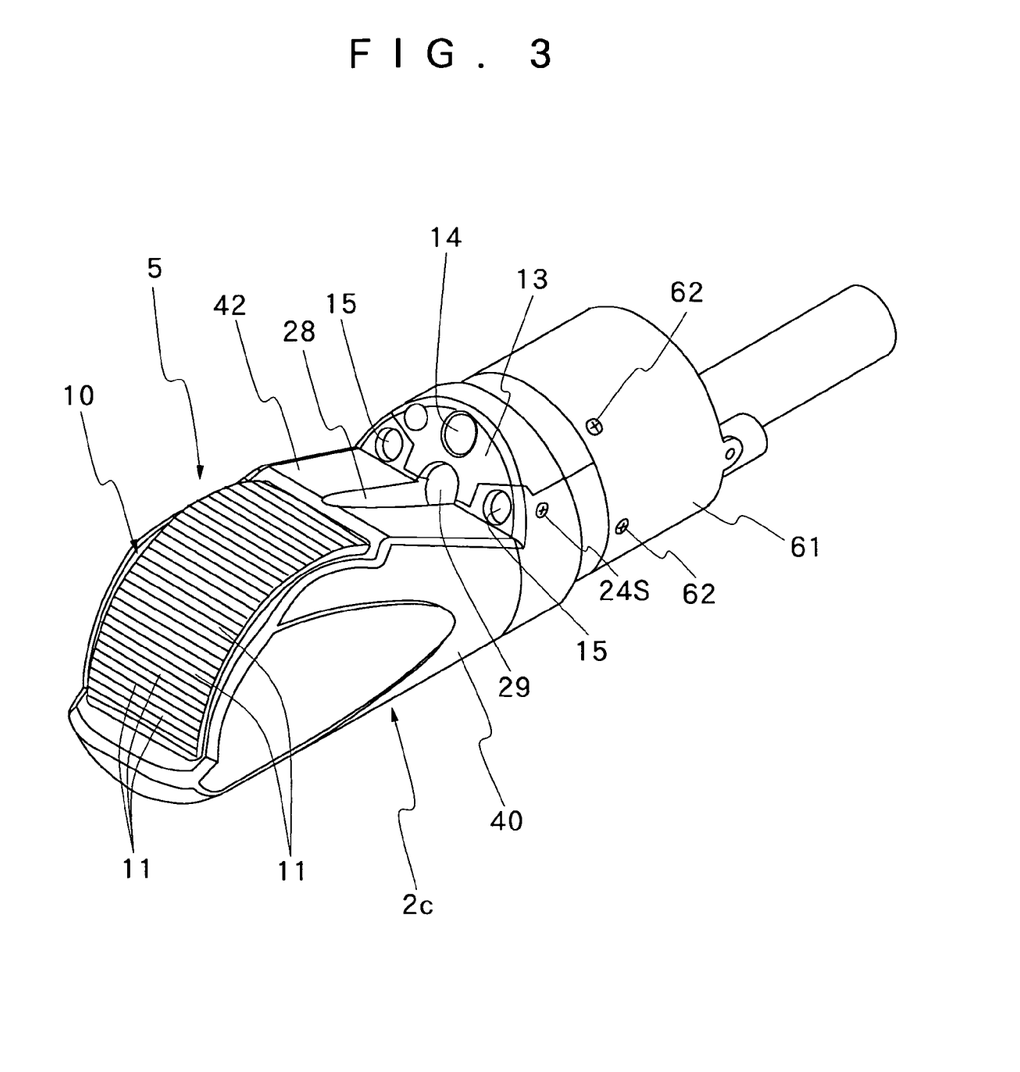
FIG. 3 is a perspective view of the rigid tip end section having a foremost angle ring fitted thereon.

Illustrated in FIG. 2 are the rigid tip end section 2c and those joint portions of the angle section 2b which are connected with the rigid tip end section 2c. Further, shown in FIG. 3 is an outer view of the rigid tip end section 2c which is separated from the angle section. As clear from these figures, the ultrasound examination means 5 is mounted in a front side portion of the rigid tip end section 2c, and the endoscopic observation means 4 is located on the proximal side of the ultrasound examination means 5.

In this instance, the ultrasound examination means 5 is provided with an ultrasound transducer 10 having an array of large number of ultrasound transducer elements 11 which are arranged in a convexly curved shape bulging out gradually from its base or rear end toward a most bulged top portion which is located substantially at an axially intermediate point. These ultrasound transducer elements 11 are formed with electrodes on the side of ultrasound signal transmission and reception surfaces as well as on surfaces on the opposite side. Wires 12 are connected separately at least to the respective electrodes on the ultrasound signal transmission and reception surfaces. Regarding the electrodes on the opposite side of the ultrasound transducer elements, wiring connections are made separately to the respective electrodes in some cases but it is the general practice to connect one or a certain number of wires to them as a common electrode. The wires 12 from the respective ultrasound transducer 10 are bundled together and passed through the insertion instrument 2 and the extended into the universal cable 3 via the manipulating head assembly 1.

The rigid tip end section 2c is built in a casing of a generally tubular shape, which is provided with a downslope portion in an axially intermediate portion immediately behind the ultrasound transducer 10, and an obliquely rising wall portion 13 rising gradually upward from the rear end of the downslope portion which is located at the lowermost point. The obliquely rising wall portion 13 serves as a wall portion for fitting and mounting endoscopic observation means. Namely, an endoscopic observation window 14 is opened at a substantially center position on the obliquely rising wall portion 13, and illumination windows 15 are opened on the right and left sides of the endoscopic observation window 14. It is not necessarily required to provide two illumination windows 15, one at each side of the observation window 14.

The sectional view in FIG. 2 is taken longitudinally through the endoscopic observation window 14 which is located centrally of the obliquely rising wall portion 13. For the endoscopic observation window 14, an observation window hole 16 is bored into the proximal end of the rigid tip end section 2c in an obliquely upward direction toward and through the obliquely rising wall portion 13. A lens tube 17 is fitted in the observation window opening 16 for an optical objective lens system including an objective lens 18, a cover glass 19 in the form of a planoconcave lens which is fitted in the fore end of the lens tube 17, and a prism 20. Further, a solid-state image sensor device 21 is located at the focus of the objective lens 18. The respective component parts which are fitted in the observation window 14 assembled and provided as an image pickup assembly unit 22. Signal lines 23 which are led out from the solid-state image sensor device 21 are bundled together and passed through the insertion instrument 2 and extended into the universal cable 3 via the manipulating head assembly 2.

Figure 4:
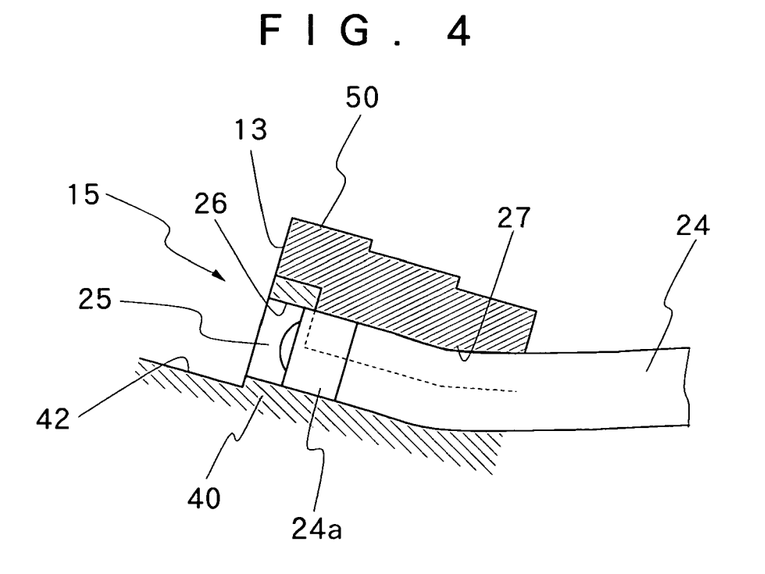
FIG. 4 is a fragmentary sectional view showing the manner in which a light guide is fitted in an illumination window on the rigid tip end section.
Figure 5:
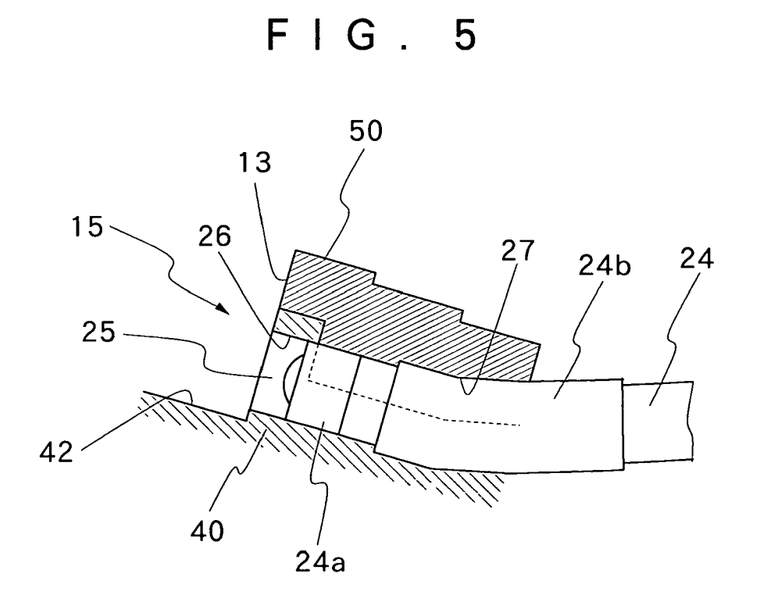
FIG. 5 is a view similar to FIG. 4 but showing another light guide which is fitted in an illumination window on the rigid tip end section in a different manner.

As seen in FIG. 4, each illumination window 15 is largely constituted by a light guide 24, which internally contains a large number of fiber optics, and a diffuser lens 25. A light emitting end of the light guide 24 is disposed in the illumination window 15, on the inner side of the diffuser lens 25 which is fitted in a lens mount hole 26 which is formed in the casing of the rigid tip end section 2c continuously at the fore end of a light guide fitting hole 27, in which the light guide 24 is fitted. In this instance, the light guide fitting hole 27 is formed in a bent shape having a sloped portion extending gradually downward over a certain length from its fore end in communication with the lens fitting hole 26 and then connected to a rear rectilinear portion which is extended in the axial direction of the rigid tip end section 2c. The light guide 24 is flexible in bending directions of the insertion instrument, and its fore end is stopped in a metal piece 24a which is in turn fixed in position by a set screw 24s. Further, in a case where the light guide 24 is fitted in a rigid pips 24b at a bent portion of the light guide fitting hole 27, the light guide 24 is securely retained in position by the rigid pipe 24b.

Further, an outlet passage 29 of the biopsy channel is opened in the obliquely rising wall portion 13, and a forwardly rising guide surface 28 is on the downslope portion on the rear side of the ultrasound transducer 10. Through the outlet passage 29, various biopsy and surgical instruments can be projected into a body cavity of a patient, including forceps or other biopsy or surgical instruments to be operated under observation by the endoscopic observation means 4 and those instruments like a puncture instrument with a puncture needle to be operated under observation by the ultrasound examination means 5. A required biopsy or surgical instrument is introduced into the biopsy channel through an inlet passage 7 which is provided in the casing of the manipulating head assembly 1. Accordingly, a biopsy channel 30 is extended from the inlet passage 7 on the manipulating head assembly 1 to the outlet passage 29 on the rigid tip end section 2c of the insertion instrument of the endoscope.

Between the inlet passage 29 and a point in the proximity of or immediately on the proximal side of the rigid tip end section 2c, the biopsy channel 30 is constituted by a flexible tube 31 which is extended axially through the insertion instrument 2. A biopsy channel outlet passage way 32 is formed within the casing of the rigid tip end section 2c. In order to connect the biopsy channel tube 31 to the outlet passage way 32, a connector pipe 33 is provided between these parts. In this instance, the outlet passage way 32 which leads to the biopsy channel outlet 29 is inclined upward toward the biopsy channel outlet 29. Therefore, the connector pipe 33 is bent in an axially intermediate portion to switch the direction of the biopsy channel in an obliquely upward direction toward the outlet opening 29 at the fore end of the biopsy channel tube 31 which is extended in the axial direction of the insertion instrument 2.

Figure 6:
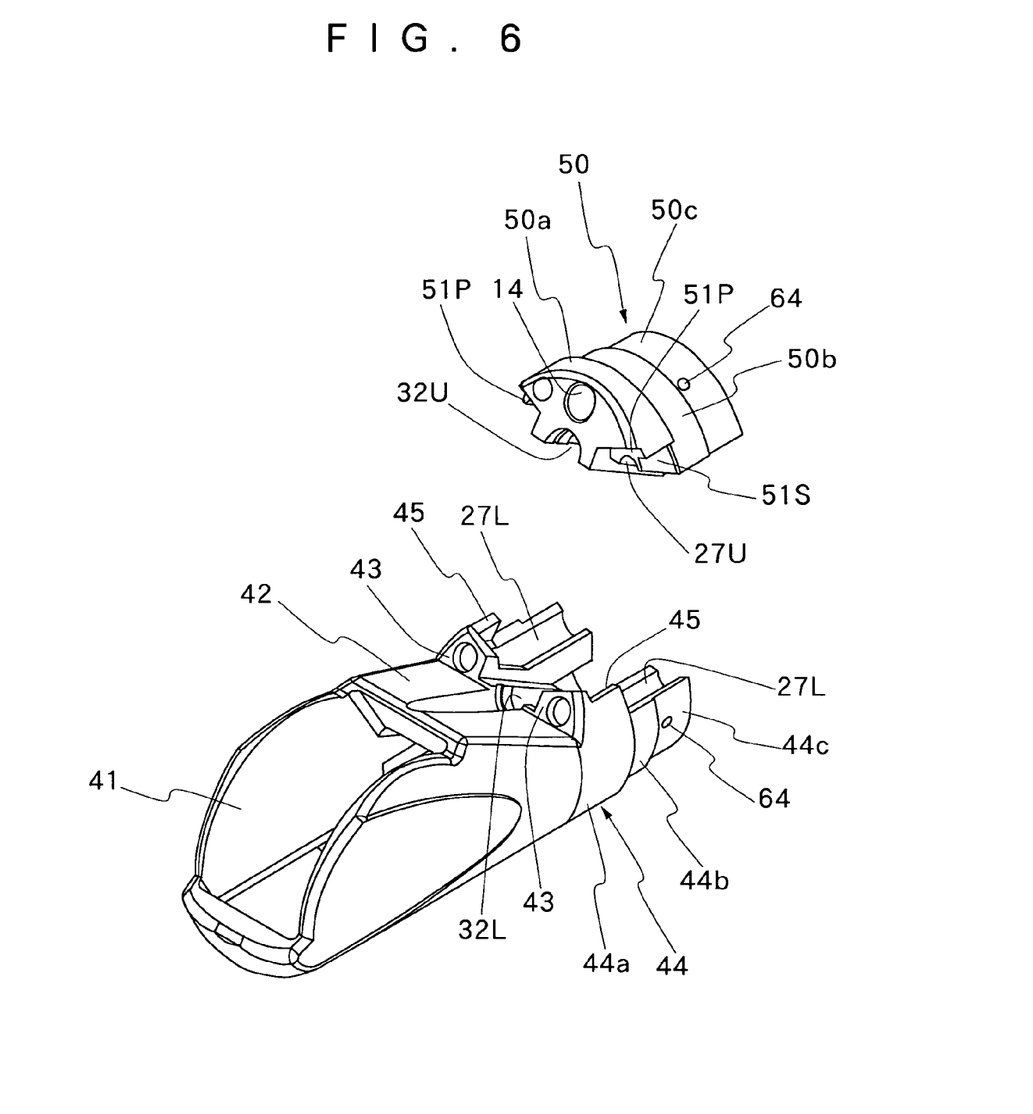
FIG. 6 is a schematic perspective view of a main casing of the rigid tip end section and a separable head block which is detached from the main casing, taken from the front side of the rigid tip end section.
Figure 7:
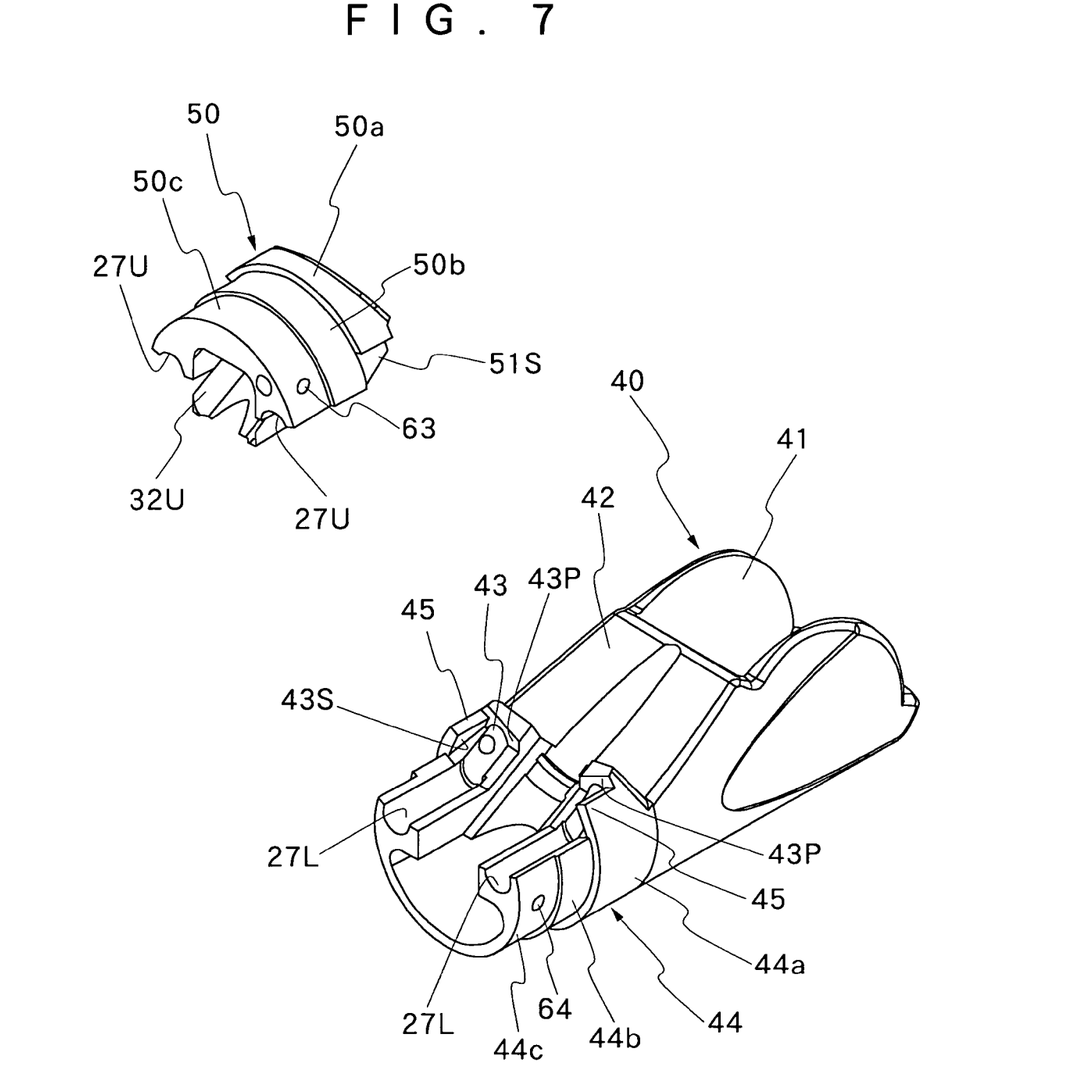
FIG. 7 is a schematic perspective view of the main casing of the rigid tip end section and a separable head block which is detached from the main casing, taken from the rear side of the rigid tip end section.

In this particular embodiment, as shown in FIGS. 6 and 7, the rigid tip end section 2c is housed in a separable casing which is composed of a main casing 40 and a separable head block 50. The main casing 40 includes a front compartment 41 for accommodating the ultrasound transducer 10, a downslope wall portion 42 which is provided on a rear section of the front compartment 41 and inclined downward toward the rear end of the rigid tip end section 2c, lens fitting wall portions rising obliquely upward from right and left side portions of the downslope wall portion 42 and provided with lens fitting portions 43 with apertures or through holes for fitting illumination light diffuser lenses 25, and a tubular neck portion 44 which is formed continuously on the rear side of the lens fitting portions 43 and configured with three stepped circumferential walls. Provided centrally of the tubular neck portion 44 is an arcuate or semi-circular groove 32L which forms a lower half of the biopsy channel outlet passage 32 leading to the outlet opening 29 of the biopsy channel. Further, provided on the right and left sides of the semi-circular groove 32L are semi-circular grooves 27L which form lower halves of the light guide fitting holes 27 leading to the apertures in the diffuser lens fitting portions 43.

The neck portion 44 is provided with three stepped circumferential wall portions, including a large diameter portion 44a which is located on the front side of the neck portion 44, and an intermediate diameter portion 44b which is sunken stepwise from the large diameter portion 44a in an extent corresponding substantially to the thickness of a skin layer of the angle section 2b which will be described more particularly hereinlater. Further, formed continuously on the rear side of the intermediate diameter portion 44b is a small diameter portion 44c. The small diameter portion 44c is sunken stepwise from the intermediate diameter portion 44b in an extent corresponding substantially to the thickness of an angle ring in the angle section 2b. Lower bottom portions of the internal space of the neck portion 44 are utilized as a passage for the wires 12 from the ultrasound transducer 10.

On the other hand, the separable head block 50 is arranged to close the open top of the neck portion 44 in such a way that the rear end of the rigid tip end section 2b generally presents a cylindrical shape. Therefore, the separable head block 50 is configured with three stepped circumferential walls, i.e., a large diameter portion 50a, an intermediate diameter portion 50b and a small diameter portion 50c conforming in diameter with the large diameter portion 44a, intermediate diameter portion 44b and small diameter portion 44c of the tubular neck portion 44, respectively. Further, formed on the inner side of the separable head block 50 is a semi-circular groove 32U which forms the upper half of the biopsy channel outlet passage 32 leading to the outlet opening 31 of the biopsy channel 30. Furthermore, formed on the right and left sides of the semi-circular groove 32U are semi-circular grooves 27U which form upper halves of the light guide fitting holes 27.

As described above, the light guide fitting hole 27 and the biopsy channel outlet passage 32 are constituted by the semi-circular grooves 27L, 27U, 32L and 32U which are formed opposingly on the neck portion 44 and the separable head block 50. These semi-circular grooves 27L, 27U, 32L and 32U are provided joining surfaces on the opposing side wall portions to be engaged tightly with each other. Further, the fore end face of the separable head block 50 is abutted against circumferential wall portions of the lens fitting portions 43 on the side of the main casing 40. More particularly, joining wall sections 43P are provided on the inner side of the lens fitting portions 43 of the main casing 40 for engagement with opposing joining wall sections 51P which are provided on right and left fore end portions of the large diameter portion 50a of the separable head block 50. Formed at one side of these joining wall sections 43P and 51P on the main casing 40 and the separable head 11 block 50 are interlocking portions 43S and 51S each with a tapered surface (or an arcuate surface) which is inclined obliquely outward in the downward direction. As these interlocking portions 43S and 51S are engaged with each other, the separable head block 50 is restricted of movements not only in lateral rightward and leftward directions but also in a direction away from the main casing 40 of the rigid tip end section.

Accordingly, at the time of fitting the separable head block 50 in the main casing 40 of the rigid tip end section, the interlocking portions 51S of the separable head block 50 are slid into the inner side of the interlocking portions 43S on the side of the main casing 40 from the rear side of the latter until the joining wall sections 43P and 51P come into abutting engagement with each other. Whereupon, the rigid tip end portion 2c is assembled as shown in FIG. 3. At the time of joining the separable head block 50 with the main casing 40 of the rigid tip end section 2c, it is desirable to apply either weakly adhesive seal material or non-adhesive seal material around joined portions to keep the internal space of the rigid tip end section in a hermetically sealed state.

The rigid tip end section 2c is required to accommodate, in addition to the ultrasound transducer 10 and the wires 12 from the respective ultrasound transducer elements 11, the image pickup assembly unit 22 in the endoscopic observation window 14, the light guides 24 to the illumination windows 15, and the connector pipe 33 which connects the biopsy channel tube 31 to the biopsy channel outlet passage in the casing 40. Among the various component parts just mentioned, the ultrasound transducer 10 including the wires 12 and the image pickup assembly unit 22 are built in the main casing 40 and the separable head block 50 beforehand, respectively.

On the other hand, the light guides 24 and connector pipe 33 are fitted into respective positions when the separable head block 50 is assembled with the main casing 40. More particularly, the light guides 24 are placed in the semi-circular grooves 27L on the side of the main casing 40, and then the separable head block 50 is joined with the main casing 40. Whereupon the semi-circular grooves 27U on the separable head block 50 are closed on the light guides 24 in the lower semi-circular grooves 27L of the light guide fitting holes 27. The light guides 24 are fixed in position by set screws 24S. Each light guide 24 can be fixedly retained in position because the rigid pipe 24b is set in the bent portion of the light guide fitting hole 27.

The connector pipe 33 also contains a bent portion so that it can be fixed in both radial and axial directions if it is extended beyond a bent portion of the biopsy channel outlet passage in a manner similar to the light guide 24. In the particular embodiment shown, as shown in FIG. 2, a stopper notch 46 is provided within the length of the lower or upper semi-circular groove 32L (or 32U) which is formed on the main casing 40 (or on the separable head block 50) as a lower or upper part of the biopsy channel outlet passage 32. A stopper protuberance 52 is provided on the side of the connector pipe 33 for fitting engagement with the stopper notch 46 in the semi-circular groove 32L or 32U. Accordingly, the stopper protuberance 52 is engaged with the stopper notch 46 at the time of placing the connector pipe 33 in the semi-circular groove 32L, which is the lower part of the biopsy channel outlet passage 32. Then the separable head block 50 is joined with the main casing 40. As soon as the separable head block 50 is set in position on the main casing 40, the connector pipe 33 is fixed in position and its spontaneous movement 11 is blocked in both radial and axial directions.

Even if various component parts have been assembled into the rigid tip end section 2c in the manner as described above, the main casing 40 and the separable head block 50 are not yet strongly fixed to each other although seal material is applied at joined portions. As shown in FIGS. 2 and 3, the main casing 40 and the separable head block 50 are securely fixed to each other by means of a foremost ring member 61 in a series of angle rings 60 which constitute the angle section 2b of the insertion instrument 2.

Figure 8:
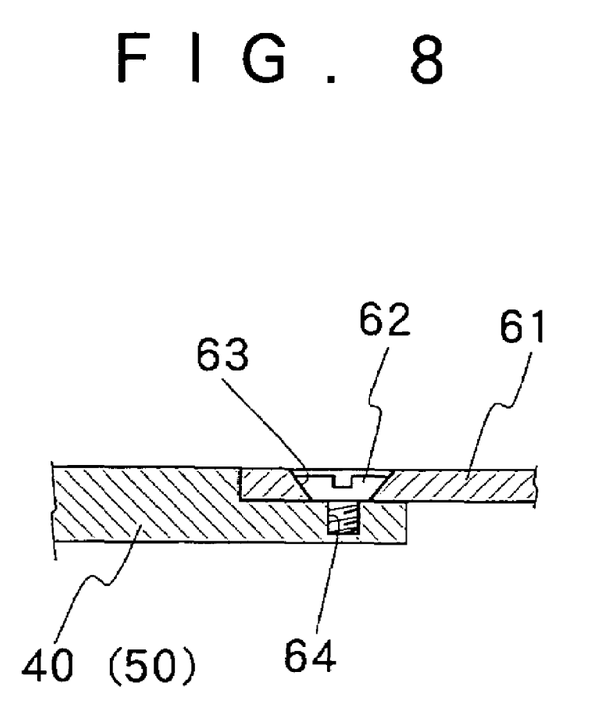
FIG. 8 is a fragmentary sectional view showing the manner in which an end ring is assembled with the main casing of the rigid tip end section.

After joining the separable head block 50 with the neck portion 44 of the main casing 40, the above-mentioned foremost ring member 61 is fitted on the small diameter portions 44c and 50c of the main casing 40 and the separable head block 50. Then, as shown also in FIG. 8, the foremost ring member 61 is fixed to both of the main casing 40 and separable head block 50 by the use of at least one flat head screw 62. For this purpose, a number of tapered holes 63 are formed into the outer peripheral surface of the foremost ring 61 at suitable angular intervals and at suitable positions relative to screw holes 64 which are tapped into the small diameter portion 44c of the 11 neck portion 44 of the main casing 40 and the separable head block 50. By tightening the flat head screws 62 into the screw holes 64 through the tapered holes 63 in the foremost ring member 61, the main casing 40 and the separable head block 50 are completely restricted of spontaneous movements not only in forward and backward directions but also in a separating direction away from each other. In addition, the main casing 40 and the separable head block 50 are virtually integrally joined together in such a way as to prevent relative positional deviations not only in radial and axial directions but also in a separating direction.

In this connection, it is not necessarily required for the fitting portion of the foremost ring member 61 to have a function as a seal. However, arrangements may be made to bond the foremost ring member 61 in position with a moderate adhesive power, permitting to detach the ring member 61 afterwards relatively easily whenever the necessity arises. A flexible outer skin layer 65, with flexibility in stretching and bending directions, is fitted around the angle section 2b in such a manner as to cover the entire angle rings 60 including the foremost ring member 61. The outer skin layer 65 is extended forward of the angle section 2b beyond the fore end of the foremost ring member 61 and onto the intermediate diameter portions 44b and 50b of the neck portion 44 and the separable head block 50. A fore end portion of the outer skin layer 65 is fixedly anchored on the intermediate diameter portions 41b and 50b by applying an adhesive around line wrapping 66.

The above-described construction of the rigid tip end section makes it possible to inspect, repair and replace internal component parts of the insertion instrument 2 in an extremely facilitated manner. For maintenance and service of internal component parts, disassembling of the rigid tip end section 2c is started by removing the adhesive and line wrapping 66 from around the outer skin layer 65, and then the outer skin layer 65 is tucked backwards toward the angle section 2b with fingers until the foremost ring member 61 is completely exposed. In this state, the flat head screws to permit separation of the separable head block 50 from the main casing 40 of the rigid tip end section 2c. Up to this point, there is no difference in particular from the prior art in terms of disassembling procedure.

Upon removing the flat head screws 62, the rigid tip end section 2c can be split into the main casing 40 and the separable head block 50. Besides, upon splitting the rigid tip end section 2c, the connector pipe 33 in the biopsy channel outlet passage 32 can be detached independently. Therefore, if necessary, the flexible biopsy channel tube 31 can be easily removed from the connector pipe 31 and replaced by a new one. In this connection, taking into consideration the fact that inner surfaces of the biopsy channel tube 31 which is repeatedly used for introduction of a puncture instrument are susceptible to damages and buckling, it is important and advantageous to make the biopsy channel tube 31 easily accessible for replacements. This maintenance and service work can be carried out without removing, relocating or touching other component parts, especially the ultrasound transducer 10 which is built in the main casing 40 along with the wires 12.

Similarly, the light guides 24 can be taken out independently of other component parts. Breakage could occur to the light guide 24 which is comprised of fiber optics. However, in case of breakage, it can be easily replaced. Furthermore, the optical image pickup assembly unit 22 is fixedly assembled with the separable head block 50. Therefore, upon detaching the separable head block 50 from the main casing 40, the solid-state image sensor device 21 and signal lines 23 are exposed on the inner side of the separable head block 50 and are easily accessible for an inspection or repair work or for other purposes.

Upon completion of an inspection, repair or replacement work on the opened rigid tip end section 2c, the respective internal components are relocated to the respective positions before rejoining the separable head block 50 with the main casing 40. The separable head block 50 and the main casing 40 are securely fixed to each other by threading the flat head screws 62 through the foremost ring member 61. Finally, the fore end of the outer skin layer 65 is anchored by applying line wrapping and adhesive therearound to put the insertion instrument 2 back into the initial closed and sealed state.

In the above-described embodiment, the separate block 50 is arranged to be separable from the main casing 40 along a split line which is located at the position of or across the biopsy channel outlet passage 32 especially for the purpose of facilitating replacements of the biopsy channel tube 31 among various internally fitted component parts of the insertion instrument. However, in a case where maintenance and service of the optical image pickup assembly unit is required at a higher frequency, it will be more convenient to arrange the main casing and the separable head block in the manner as in a modification shown in FIG. 9. In this case, a split line of a separable head block 71 so determined as to leave the biopsy channel outlet passage on the side of a main casing 70 of the rigid tip end section 2c, receiving a lens tube 72 of an optical image pickup assembly unit in an optical lens fitting hole 73 which is split into an arcuate groove 73L on the side of the main casing 70 and an arcuate groove 73U on the side of the separable head block 71. Both of these arcuate grooves 73L and 73U are semi-circular in cross-section and arranged to hold the lens tube 72 fixedly therebetween when joined with each other.

Figure 9:
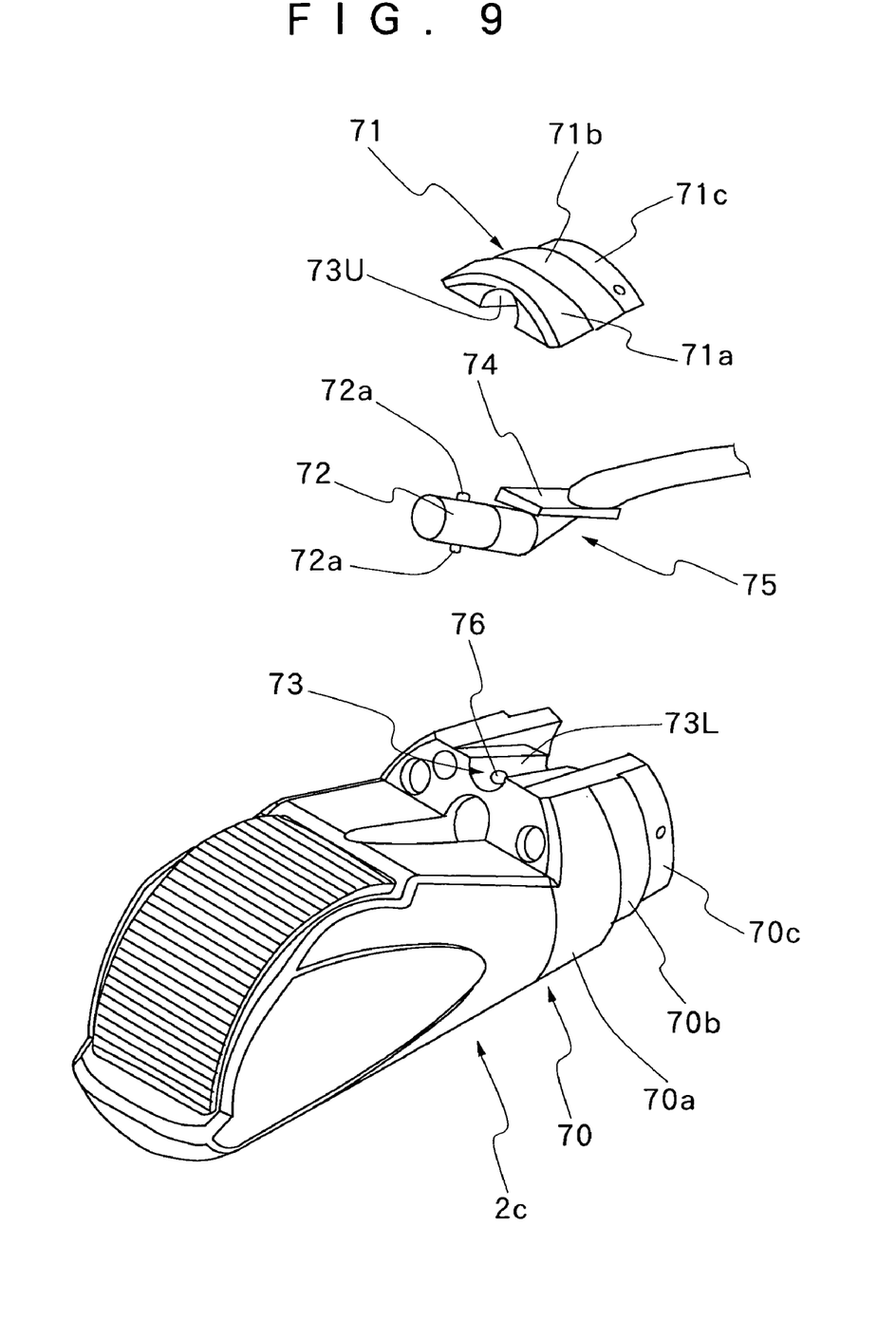
FIG. 9 is a perspective view of a rigid tip end section according to a second embodiment of the invention, taken from the front side, showing a main casing and a separable head block which is separated from the main casing.

Similarly to the main casing 40 and separable head block 50 in the foregoing first embodiment, large diameter portions 70a and 71a, intermediate diameter portions 70b and 71b and small diameter portions 70c and 71c are provided on a neck portion of the main casing 70 and the separable head block 71. A foremost ring member of the angle section is fitted on the small diameter portions 70c and 71c and the joined main casing 70 and separable head block 71 are securely fixed to each other by flat head screws in the same manner as in the above-described first embodiment. Further, a fore end of an outer skin layer of the angle section 2b is extended onto the intermediate diameter portions 70b and 71b and fixedly anchored thereon in the same manner as in the first embodiment.

Assembled with the lens tube 72 are solid-state image sensor device 74 and other parts which constitute an optical image pickup assembly unit 75. Since the lens tube 72 is assembled with the solid-state image sensor device 74, it has to be fixed in the rotational direction. Therefore, a pair of stopper projections 72a are provided on the outer periphery of the lens tube 72, for engagement with notches 76 which are provided in corresponding positions in the arcuate grooves 73L and 73U, which are provided on the main casing 70 and the separable head block 71 to form the lens tube fitting hole 73 (a notch in the arcuate groove 73U is not seen in the drawing). As a consequence, in an assembled state, there is no possibility of spontaneous positional deviations occurring to the separable head block 71 and the image pickup assembly unit 75. At the time of replacing the image pickup assembly unit 75, the separable head block 71 is detached from the main casing in the same manner as in the foregoing first embodiment. Whereupon, the image pickup assembly unit 75 can be detached from the rigid tip end section 2c separately and independently of the main casing 70 and the separable head block 71. Accordingly, even in this case, there is no possibility of damaging the ultrasound transducer 10 and its wiring 10 in carrying out maintenance and service on the image pickup assembly unit 75.

As clear from the foregoing description, the rigid tip end section of an endoscopic insertion instrument is constituted by a main casing and a separable head block which is separably joined with the main casing. The provision of the rigid tip end section which can be split into the main casing and separable head block make it extremely easy to carry out maintenance and service, including inspection, repair and replacements, of internally fitted component parts of the rigid tip end section of the insertion instrument.

What is claimed is:

1. An ultrasound endoscope having a rigid tip end section connected to a fore end of an angle section at the distal end of an insertion instrument for accommodating an ultrasound transducer along with endoscopic observation means including an illumination means and an optical image pickup assembly unit;

said ultrasound transducer being accommodated in a front portion of a generally tubular casing of said rigid tip end section, said endoscopic observation means being fitted in a sloped wall section provided on said casing on the rear side of said ultrasound transducer and inclined obliquely upward in the rearward direction, and an outlet opening of a biopsy channel outlet passage being opened in said casing at a position between said endoscopic observation means and said ultrasound transducer:

wherein:

said casing of said rigid tip end section is separable into a main casing adapted to accommodate entire parts of said ultrasound transducer and a separable head block adapted to accommodate at least part of component parts of said endoscopic observation means and separably joined with said main casing to form a cover over an opening provided in said main casing behind said ultrasound transducer and through part of said sloped wall section;

said head block is joined with said main casing at joining wall portions provided on said main casing and said separable head block at opposite sides of said optical endoscopic observation means;

a foremost ring member of angle rings in said angle section is removably fitted on base end portions of said main casing and said separable head block; and a fore end of an outer skin layer of said angle section is extended forward beyond said foremost ring member and fixedly anchored on a circular outer skin layer anchor surface provided around joined base end portions of said main casing and said separable head block.

2. An ultrasound endoscope as defined in claim 1, wherein said biopsy channel outlet passage is inclined obliquely upward in the forward direction toward an outlet opening on said rigid tip end section, a connector pipe from a biopsy channel tube is fitted and gripped in a rear end portion of said biopsy channel outlet passage formed by joining upper and lower semi-circular grooves provided on said separable block and said main casing, respectively.

3. An ultrasound endoscope as defined in claim 2, wherein both of said biopsy channel outlet passage and said connector pipe are arcuately bent at an axially intermediate portion.

4. An ultrasound endoscope as defined in claim 2, wherein said separable head block is adapted to accommodate said illumination means and optical image pickup assembly unit of said endoscopic observation means.

5. An ultrasound endoscope as defined in claim 2, wherein said illumination means has a light guide fitting hole formed by joining semi-circular grooves provided on said separable head block and said main casing, respectively, a diffuser lens is fitted in a lens fitting hole provided on said main casing at a front end of said light guide fitting hole.

6. An ultrasound endoscope as defined in claim 1, wherein said optical image pickup assembly unit of said endoscopic observation means has a lens tube of an optical objective lens system, said lens tube of said objective lens system being fitted in a sloped lens tube fitting hole provided on said rigid tip end section, said lens tube fitting hole being inclined upward in the forward direction and formed by joining upper and lower semi-circular grooves provided on said separable head block and said main casing of said rigid tip end section.

7. An ultrasound endoscope as defined in claim 6, wherein said lens tube of said optical image pickup assembly unit is locked in position in said lens tube fitting hole by stopper projections and notches provided in corresponding positions on said lens tube and said semi-circular groove on the side of said main casing.

8. An ultrasound endoscope as defined in claim 1, wherein said main casing and said separable head block are securely fixed with each other by the use of screws.

9. An ultrasound endoscope as defined in claim 1, wherein said main casing and said separable head block are joined with each other and securely fixed relative to each other by screws threaded thereinto through said foremost ring member of said angle section.

10. An ultrasound endoscope as defined in claim 1, wherein said main casing and said separable head block are joined with each other through seal material.

11. An ultrasound endoscope comprising:

an insertion instrument accommodating an ultrasound transducer and an endoscopic observation device, said endoscopic observation device including an illumination device and an optical image pickup assembly unit;

an angle section provided at a distal end of said insertion instrument; and a tip end section connected to a fore end of said angle section, said tip end section including:

a casing having a front portion accommodating said ultrasound transducer, a sloped wall section provided rearward of said front portion and accommodating at least a portion of said endoscopic observation device, and an outlet opening of a biopsy channel outlet passage, wherein said casing includes:

a main casing including said front portion accommodating said ultrasound transducer;

a head block separably joined to said main casing, said head block including a portion of said sloped wall section that accommodates said portion of said endoscopic observation device; and a ring member removably fitted around outer ring fitting surfaces of said main casing and said head block in order to join said main casing and said head block together, wherein said main casing has a first outlet portion and said head block has a second outlet portion, said first outlet portion and said second outlet portion together form either said outlet opening of said biopsy channel outlet passage or an opening for said endoscopic observation device, and wherein said fore end of said angle section has an outer skin layer that extends forward beyond said outer ring fitting surfaces and is fixedly anchored on circular outer skin layer anchor surfaces provided around base end portions of said main casing and said head block.

12. A tip end section of an ultrasound endoscope, said tip end section comprising:

a casing having a front portion configured to accommodate an ultrasound transducer, a sloped wall section provided rearward of said front portion and configured to accommodate at least a portion of an endoscopic observation device, and an outlet opening of a biopsy channel outlet passage, wherein said casing includes:
- a main casing including said front portion configured to accommodate the ultrasound transducer;
- a head block separably joined to said main casing, said head block including a portion of said sloped wall section that is configured to accommodate the portion of the endoscopic observation device; and
- a ring member removably fitted around outer ring fitting surfaces of said main casing and said head block in order to join said main casing and said head block together,
- wherein said main casing has a first outlet portion and said head block has a second outlet portion, said first outlet portion and said second outlet portion together form either said outlet opening of said biopsy channel outlet passage or an opening configured for the endoscopic observation device.

13. A tip end section of an ultrasound endoscope as defined in claim 12, wherein:
said first outlet portion and said second outlet portion together form said outlet opening of said biopsy channel outlet passage;
said main casing has a first semi-circular groove and said head block has a second semicircular groove; and
said first semi-circular groove and said second semi-circular groove together are configured to grip a connector pipe from a biopsy channel tube.

14. A tip end section of an ultrasound endoscope as defined in claim 12, wherein said head block is configured to accommodate an illumination device and an optical image pickup assembly unit of the endoscopic observation device.

15. A tip end section of an ultrasound endoscope as defined in claim 14, wherein:
said main casing has a first semi-circular groove and said head block has a second semicircular groove; and
said first semi-circular groove and said second semi-circular groove together form a light guide fitting hole having a front end with a lens fitting hole formed therein that is configured to receive a diffuser lens.

16. A tip end section of an ultrasound endoscope as defined in claim 12, wherein:
said first outlet portion and said second outlet portion together form said opening configured for the endoscopic observation device;
said main casing has a first semi-circular groove and said head block has a second semicircular groove; and
said first semi-circular groove and said second semi-circular groove together form a sloped lens tube fitting hole are configured to receive an optical image pickup assembly unit of the endoscopic observation device.

17. A tip end section of an ultrasound endoscope as defined in claim 16, wherein said first semi-circular groove of said main casing has a stopper notch configured to receive a stopper projection on the optical image pickup assembly unit to lock the optical image pickup assembly unit in position in said sloped lens tube fitting hole.

18. A tip end section of an ultrasound endoscope as defined in claim 12, wherein said main casing and said head block are securely fixed together with screws.

19. A tip end section of an ultrasound endoscope as defined in claim 18, wherein said screws are threaded through said ring member.

20. A tip end section of an ultrasound endoscope as defined in claim 12, wherein said main casing and said head block are joined together with seal material.

* * * * *